(12) United States Patent
Therre et al.

(10) Patent No.: US 6,518,464 B2
(45) Date of Patent: Feb. 11, 2003

(54) CONTINUOUS PROCESS FOR THE PREPARATION OF ACETALS

(75) Inventors: Jörg Therre, Worms (DE); Gerd Kaibel, Lampertheim (DE); Werner Aquila, Mannheim (DE); Günter Wegner, Römerberg (DE); Hartwig Fuchs, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/945,642

(22) Filed: Sep. 5, 2001

(65) Prior Publication Data

US 2002/0035298 A1 Mar. 21, 2002

(30) Foreign Application Priority Data

Sep. 7, 2000 (DE) .......................................... 100 44 352

(51) Int. Cl.⁷ .............................................. C07C 43/02
(52) U.S. Cl. ......................... 568/596; 568/591; 568/592
(58) Field of Search .................................. 568/591, 592, 568/596

(56) References Cited

U.S. PATENT DOCUMENTS

| 2,501,144 A | 3/1950 | Saunders ..................... 260/601 |
| 4,133,836 A | 1/1979 | Nissen et al. ................ 568/596 |

FOREIGN PATENT DOCUMENTS

| DE | 26 25 074 | 12/1977 |

*Primary Examiner*—Sreeni Padmanabhan
(74) *Attorney, Agent, or Firm*—Keil & Weinkauf

(57) ABSTRACT

The present invention relates to a continuous process for the preparation of unsaturated acetals by reacting olefinically unsaturated aliphatic compounds with allyl alcohols in a reaction column, where the reactants are only partially reacted in the reaction column, the resulting acetal is concentrated in at least two successive evaporation stages, and the recovered reactants are returned to the reaction column.

14 Claims, 1 Drawing Sheet

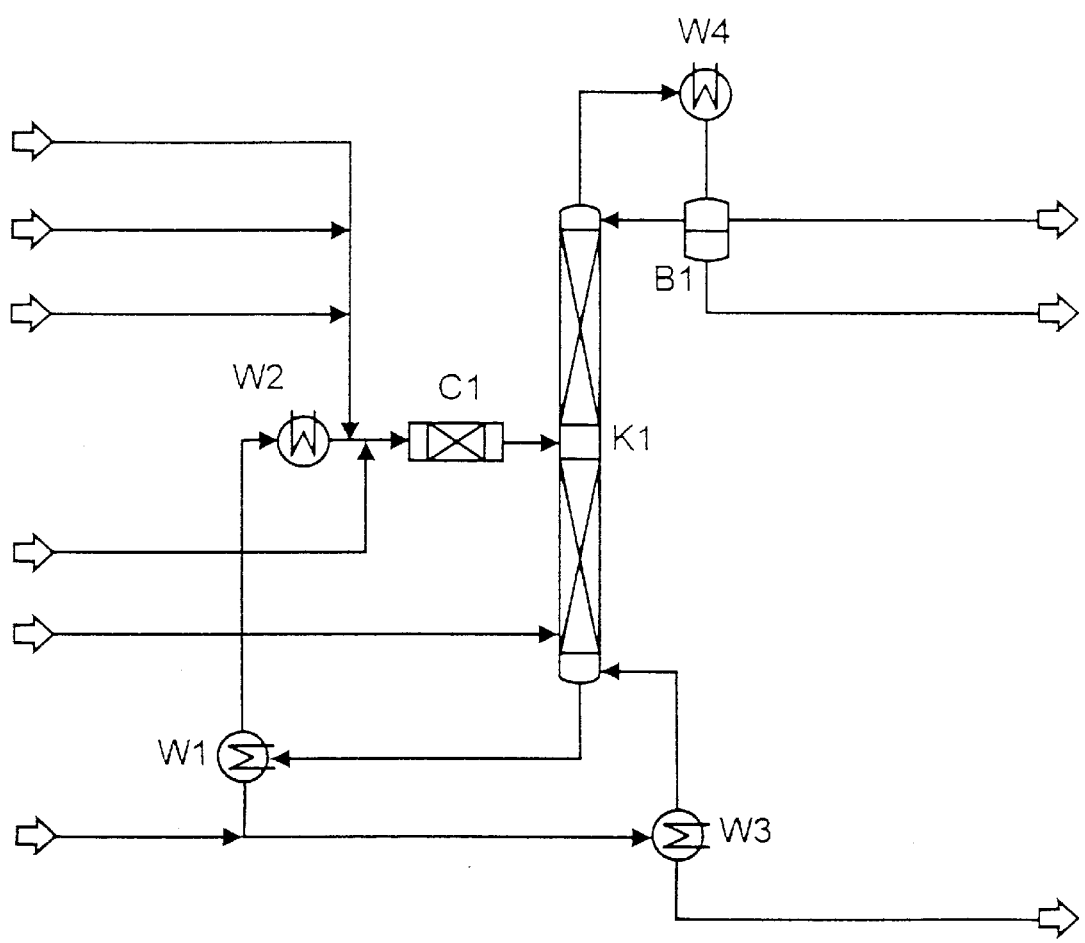

CONTINUOUS PROCESS FOR THE PREPARATION OF ACETALS

The present invention relates to a continuous process for the preparation of unsaturated acetals by reacting olefinically unsaturated aliphatic compounds with allyl alcohols in a reaction column, where the reactants are only partially reacted in the reaction column, the resulting acetal is concentrated in at least two successive evaporation stages, and the recovered reactants are returned to the reaction column.

The preparation of unsaturated acetals by reacting only olefinically unsaturated aliphatic compounds with allyl alcohols in a reaction column in the presence of a distillable acid is known per se from DE 26 25 074. There it is described that a mixture of at least 2 mol of the alcohol and one mole of the aldehyde are to be introduced into the reaction column, and the water formed during the reaction is to be distilled off overhead and stripped off using a phase separator. The acetal is then to be removed as a crude product from the evaporator of the column. The reaction column should be operated such that aldehyde is no longer present in the still discharge from the column, i.e. the aldehyde is reacted completely in the reaction column. In the examples, conversions for the aldehyde of more than 94.5% are mentioned.

The process described represents a significant advance for the preparation of acetals, but unfortunately has a number of disadvantages. Since, according to the known prior art, high conversions of more than 90% are strived for, the production plant can only be regulated with difficulty. Slight variations in the amount of feed streams or in the purities of the feed substances mean that the desired conversion in the reaction column cannot be maintained. This circumstance is particularly notable when contaminated feed substances are used. Such impurities are e.g. secondary products of the aldehyde and of the alcohol, such as, for example, formates of the alcohol, ethers formed from the alcohol, or condensation products from alcohol and aldehyde linked via C—C bonds. As is known, such by-products form in a relatively large amount particularly when the acetal is subjected to a cleavage and rearrangement reaction in accordance with Claisen and Cope, as is the case, for example, during the preparation of citral.

The addition of the correct amount of acid has proven particularly difficult. Even a slight deficit of the acid can lead to breakdown of the conversion in the reaction column. However, the addition of more than the correct amount of acid leads to a considerable increase in the amount of high-boiling secondary components and ethers. Regulation of the amount of acid is made more difficult by the fact that the acid accumulates in the reaction column and, as a result, the addition of too much or too little is only noticed after a considerable delay in time.

The abovementioned disadvantages have hitherto prevented the economic preparation of the acetals in the reaction column on an industrial scale.

It is an object of the invention to overcome said disadvantages and to provide a process for the preparation of unsaturated acetals which is easy to regulate and can be operated in a stable manner.

We have found that this object is achieved according to the invention by a process for the preparation of unsaturated acetals of the formula I

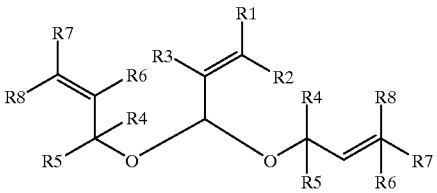

(I)

in which
R1 to R7 independently of one another are hydrogen, a straight-chain or branched, optionally substituted $C_1$–$C_6$-alkyl radical and
R8 is hydrogen, a saturated or a mono- or polyunsaturated, straight-chain or branched, optionally substituted $C_1$–$C_{12}$-alkyl radical or an optionally substituted 3- to 12-membered saturated or a mono- or polyunsaturated carbocycle, by reacting one mole of an aldehyde of the formula II

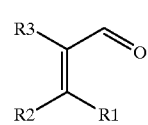

(II)

in which R1 to R3 are as defined above, with at least 1 mol of an alcohol of the formula III

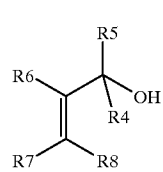

(III)

in which R5 to R8 are as defined above, in the presence of catalytic amounts of acid and with removal of the water formed during the reaction, which comprises only partially reacting the reactants in a reaction column, concentrating the resulting acetal in at least two successive evaporation stages, and returning the recovered reactants to the reaction column.

A straight-chain or branched $C_1$–$C_6$-alkyl radical is understood as meaning, for example, a methyl, ethyl, propyl, isopropyl, butyl, tert-butyl, pentyl or hexyl radical, preferably a methyl or isopropyl radical.

A saturated or mono- or polyunsaturated straight-chain or branched $C_1$–$C_{12}$-alkyl radical is understood as meaning, for example, a methyl, ethyl, propyl, isopropyl, butyl, tert-butyl, pentyl, hexyl, allyl, ethylene, propylene, butylene, isobutylene, pentenyl, hexenyl, heptenyl, octenyl, decenyl, acetylene, propinyl, butinyl, butadienyl, isoprenyl or the hexadienyl radical, preferably the methyl or pentenyl radical.

A 3- to 12-membered saturated or mono- or polyunsaturated carbocycle is understood as meaning, for example, a cyclopropyl, cyclobutanyl, cyclopentyl, cyclohexyl, cycloheptyl, cyclooctene, cyclohexene, cyclopentene, cyclooctadiene, cyclooctatetraene or a cyclododecatriene radical.

The substituents of a carbocyclic ring system or of an alkyl radical are understood as meaning, for example, halogen, nitro, cyano, hydroxyl, $C_1$–$C_6$-alkyl, $C_1$–$C_6$-alkoxy, $C_1$–$C_6$-alkoxycarbonyl or amino.

Alkoxy groups are, in combination with an alkyl group according to the above definition, with an oxygen atom, e.g. methoxy, ethoxy, propoxy, isopropoxy, butoxy or pentoxy, preferably methoxy.

Aldehydes of the formula II which may be used are, for example, acrolein, 2-buten-1-al, 2-methyl-2-buten-1-al, 3-methyl-2-buten-1-al, 2-methyl-4-methoxy-2-buten-1-al, 2-methyl-4-methoxy-2-buten-1-al, 3-isopropyl-2-buten-1-al. Of particular importance for further syntheses are acetals derived from 3-methyl-2-buten-1-al.

Alcohols of the formula III which are suitable according to the invention are, for example, 2-propen-1-ol, 2-buten-1-ol, 2-methyl-3-buten-2-ol, 3-methyl-2-buten-1-ol, geraniol, 2-methyl-2-propen-1-ol, preferably 3-methyl-2-buten-1-ol (prenol).

The acetals produced by the process of the invention are valuable starting materials for plastics, active ingredients, fragrances and vitamins. For example, 1,1-bis(3-methyl-2-buten-1-yloxy)-3-methyl-2-butene (3-methyl-2-butenal diprenyl acetal) is an important starting compound for the fragrance citral.

BRIEF DESCRIPTION OF THE DRAWING

The process is shown diagrammatically in the FIG. 1 and is described below.

The apparatus consists of a distillation column K1 which is used as a reaction column. The vapors which rise to the top of the column are condensed in the condenser W4 and passed to a phase separation vessel B1, where the water separates out as the lower phase. The upper phase consists essentially of organic compounds (aldehyde, alcohol and low-boiling secondary compounds, e.g. the formates of the alcohol used). The majority of the organic phase is returned to the top of the column K1 as reflux, and a minor fraction is bled from the system to remove the secondary components.

The amount of reflux per 1000 kg of freshly added aldehyde is 200 kg to 50 000 kg, in particular 1000 kg to 20 000 kg. This small amount of reflux and thus the low energy requirement represents a particular advantage of the process according to the invention.

The amount bled from the system is between 1 kg and 400 kg, in particular between 5 kg and 200 kg, per 1000 kg of freshly added aldehyde, depending on the purity of the feed substances used.

The still discharge from the column passes into the evaporator W1, which represents the first stage of the two-stage concentration of the acetal.

The vapors obtained in evaporator W1 consists of 10% by weight to 80% by weight of alcohol, up to 10% by weight of the acetal and 10% by weight to 40% by weight of the aldehyde. The conversion of aldehyde in the reaction column is thus less than 90%. It is possible to dispense with the condensation of the vapors and to expedite the return of the vapors in gaseous form to the column K1. However, the vapors are preferably condensed in the condenser W2.

The amount of vapors produced in the evaporation stage W1, i.e. the amount of reactants returned to the first evaporator stage, is between 2 and 30 times, in particular between 3 and 20 times, the amount of freshly added aldehyde. Too low an amount of the reactants returned to the first evaporation stage leads to a loss in selectivity. Too high an amount of the reactants returned to the first evaporation stage, although favorable for the selectivity of the acetal synthesis, consumes unnecessarily high amounts of energy. A great advantage of the process according to the invention is the ready regulatability and stable operation since the amount of reactants to be returned to the first evaporation stage can be readily determined by observing the temperatures in the column K1 and the evaporators W1 and W3.

Where appropriate, a reactor C1 can be used into which the condensate obtained in the condenser W2 and the feed materials alcohol and aldehyde are added. The reactor C1 serves to establish the thermodynamic equilibrium between alcohol and aldehyde on the one hand and water and acetal on the other hand. For the reactor C1 it is possible to use back-mixed reactors (such as, for example, stirred-tank reactors), but advantageously not back-mixed reactors with tubular reactor characteristics (such as, for example, with packed columns, cascaded tanks). The residence time of the reaction mixture in the reactor C1 should be between 0.1 sec and 10 hours. Since the thermodynamic equilibrium is often established very quickly, a very short residence time suffices under certain circumstances. It may then be possible to dispense with specific apparatus, and for the pipeline, which is in any case present, between the mixing site of alcohol, aldehyde and the condensate obtained in the condenser W2, to serve as reactor C1. For the mixing of the feed substances with the condensate obtained in the condenser W2, it may in some instances be possible to use the customary mixing elements, such as, for example, static mixers or stirred-tank reactors.

The acid can be added to the reactor C1 or the evaporator W1. However, preference is given to adding the acid to the reaction column K1 and there again advantageously to the lower part of the column or to the evaporator W3, if the acid is volatile and, in particular, if nitric acid is used. It is also possible to add the acid at different sites, e.g. at two or more sites in the column, or to add some to the column and some to the reactor C1. The liquid leaving the reactor should preferably be added to the upper part of the column. It is also possible to add the liquid, optionally mixed with the reflux, directly as return stream to the top of the column.

The addition site of fresh aldehyde and fresh alcohol is not critical. The two feed substances can also be added separately at different sites of the column K1 and/or the reactor C1. Preferably, the feed substances are combined with the discharge from the condenser W2. The amount of freshly added alcohol is regulated such that the ratio of alcohol to aldehyde is between 1 and 3, in particular between 1.5 and 2.5. A particular advantage of the process according to the invention is that the contaminated feed substances described above can also be used without problems.

The liquid leaving the evaporator W1 usually comprises the acetal in a concentration between 10% by weight and 70% by weight. The remainder consists essentially of the aldehyde and the alcohol. This liquid is added to the evaporator W3, and there the acetal is obtained as liquid in a concentration between 30% by weight and 99.9% by weight, in particular from 50% by weight to 95% by weight. The vapors rising from the evaporator W3 are preferably returned to the bottom of the column K1 and thus used for heating the column.

Suitable internals for the column are sheet metal packings (e.g. Sulzer 250Y), fabric packings (Sulzer BX or CY) or plates (e.g. bubble-cap trays, valve trays, panel trays). The number of theoretical separation stages in the reaction column should be between 3 and 80 and in particular between 5 and 40.

The head pressure in the column K1 is between 2 mbar and 400 mbar, but the pressure should, in particular, be chosen such that, at the top, the condensation temperature is above 0° C., preferably above 20° C. and very particularly above 35° C. The pressure in the evaporator W3 results, in the preferred embodiment of the process, from the pressure differential of column K1. The pressure in the evaporator W1 is between 2 mbar and 400 mbar.

The temperature in the reactor C1 should be between −20° C. and 100° C., in particular between 0° C. and 60° C.

The acids which may be used are acids which are nonvolatile under the reaction conditions. These acids are preferably added to the upper part of the reaction column. In the lower part of the column or before/in the evaporators W1 or W3 the added acid can then be removed again by neutralization. For this, liquid basic substances can be added, or the acidic reaction mixture can be passed over a basic ion exchanger. Suitable nonvolatile acids are inorganic or organic acids, such as, for example, sulfuric acid, hydrohalic acids, such as, for example, hydrochloric acid, perchloric acid, trifluoroacetic acid, toluene sulfonic acid, acetic acid, propionic acid, butyric acid, isobutyric acid, valeric acid, acrylic acid, or acidic salts (such as, for example, $NaHSO_4$). The acid can also be fixed as solid in the column, e.g. as acidic ion exchanger such as, for example, the Katapack column internals from Sulzer. However, preference is given to using acids which are volatile under the reaction conditions, and very particular preference is given to using nitric acid.

Where appropriate, an auxiliary may be added at the top of the column to improve the phase separation between aqueous and organic phase. Suitable auxiliaries of this type are inert substances which, in a mixture with water, have a lower boiling point than the feed substances, such as, for example, hydrocarbons (pentane, hexane, cyclohexane).

The reaction volume of the reaction column can be increased by incorporating additional tanks. In the evaporation stages too, additional volume can be provided by incorporating tanks.

EXAMPLE 1

The apparatus consists of a reaction column K1 having an internal diameter of 43 mm and filled with 1.44 m of Sulzer-CY packing. The pressure at the top of the column is 89 mbar. At the top of the column is situated a condenser W4 and a phase separation vessel B1. From the lower aqueous phase which separates out are pumped, with level regulation, 38.1 g/h, and the upper organic phase runs freely back to the top of the column K1. The amount of this reflux is measured using a mass flow meter and is 1490 g/h. The liquid discharging from the still passes into an evaporator W1. There, 2469 g/h are evaporated and the vapors are condensed in the condenser W2. The pressure in the condenser W2 is 88 mbar. To the liquid obtained in the condenser W2 are added 1.7 g/h of 0.1 mol of aqueous nitric acid, 155.5 g/h of fresh 3-methyl-2-butenal, 170.8 g/h of fresh prenol (3-methyl-2-buten-1-ol) and 225.9 g/h of a contaminated prenol. The contaminated prenol comprises 84.4% prenol, 2.2% 3-methyl-2-butenal and 13.4% impurities. The mixture is added to a reactor C1 which consists of a tube having an overall volume of 3.2 l and subdivided by 5 perforated plates. The temperature in the reactor C1 is 30° C. The liquid leaving the reactor C1 is added to the column K1 to a packing height of 0.48 m. The liquid leaving the evaporator W1 is added to the evaporator W3. The pressure in the evaporator W3 is 95 mbar. The temperature in the evaporator W3 is 110° C. The vapors rising from the evaporator W3 are passed to the bottom of the column K1. Discharging from the evaporator W3 are 514.1 g/h of liquid, which comprise 71.6% 3-methyl-2-butenal diprenyl acetal, 13.6% prenol and 1.4% 3-methyl-2-butenal. This gives a selectivity for prenol of 91.2% and for 3-methyl-2-butenal of 82.5%. There are 2.1 l of liquid in each of the evaporation stages W1 and W3.

EXAMPLE 2

The apparatus consists of a reaction column K1 having an internal diameter of 43 mm and filled with 1.44 m of Sulzer-CY packing. The pressure at the top of the column is 92 mbar. At the top of the column is located a condenser W4 and a phase separation vessel B1. From the lower aqueous phase which separates out are pumped, with level regulation, 59.1 g/h. 8.8 g/h from the organic phase are removed as bleed and the remainder of the upper organic phase runs freely back to the top of the column K1. The amount of this reflux is measured using a mass flow meter and is 1396 g/h. The liquid discharging from the still passes into an evaporator W1. There, 808 g/h are evaporated and the vapors are condensed in the condenser W2. The pressure in the condenser W2 is 90 mbar. To the liquid obtained in the condenser W2 are added 249.5 g/h of fresh 3-methyl-2-butenal, 270.5 g/h fresh prenol (3-methyl-2-buten-1-ol) and 307.3 g/h of a contaminated prenol. The contaminated prenol comprises 80.8% prenol, 1.4% 3-methyl-2-butenal and 17.8% of impurities. The mixture is added to the top of the column K1. 1.1 g/h of 1 mol of aqueous nitric acid were added to the bottom of the column K1. The liquid leaving the evaporator W1 is passed to the evaporator W3. The pressure in the evaporator W3 is 95 mbar. The temperature in the evaporator W3 is 105° C. The vapors rising from the evaporator W3 are passed to the bottom of the column K1. 759.4 g/h of liquid discharged from the evaporator W3 which comprised 70.8% 3-methyl-2-butenal diprenyl acetal, 10.2% prenol and 1.4% 3-methyl-2-butenal. This gives a selectivity for prenol of 88.0% and for 3-methyl-2-butenal of 78.0%. There are 0.4 l of liquid in each of the evaporation stages W1 and W3.

EXAMPLE 3

The apparatus described in Example 2 is used. From the phase separation vessel are removed 47.2 g/h of aqueous phase and 9.1 g/h of organic phase. The amount of reflux is 1398 g/h. In the evaporator W1, 2128 g/h are evaporated. 199.7 g/h of fresh 3-methyl-2-butenal, 190.0 g/h of fresh prenol and 298 g/h of a contaminated prenol are added, and the mixture is added to the top of the column K1. The contaminated prenol comprised 79.4% prenol, 2.2% 3-methyl-2-butenal and 18.4% impurities. In the evaporator W3, 2.5 g/h of a 0.3% strength by weight nitric acid were added. The temperature in the evaporator W3 was 100.1° C. From the evaporator W3 discharge 632.1 g/h of liquid which comprised 72.9% of 3-methyl-2-butenal diprenyl acetal, 12.0% prenol and 1.6% 3-methyl-2-butenal. This gives a selectivity for prenol of 94.7% and for 3-methyl-2-butenal of 82.7%. There is 1.0 l of liquid in each of the evaporation stages W1 and W3.

We claim:
1. A process for the preparation of unsaturated acetals of the formula I

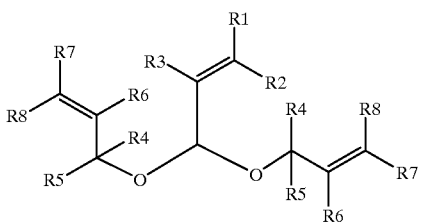

(I)

in which
R1 to R7 independently of one another are hydrogen, a straight-chain or branched, optionally substituted $C_1$–$C_6$-alkyl radical and R8 is hydrogen, a saturated or a mono- or polyunsaturated, straight-chain or branched, optionally substituted $C_1$–$C_{12}$-alkyl radical or an optionally substituted 3- to 12-membered saturated or a mono- or polyunsaturated carbocycle, by reacting one mole of an aldehyde of the formula II

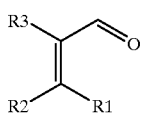

(II)

in which R1 to R3 are as defined above, with at least 1 mol of an alcohol of the formula III

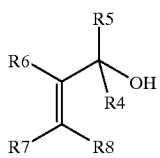

(III)

in which R5 to R8 are as defined above, in the presence of catalytic amounts of acid and with removal of the water formed during the reaction, the improvement comprising only partially reacting the reactants in a reaction column, concentrating the resulting acetal in at least two successive evaporation stages, and returning the recovered reactants to the reaction column.

2. A process as claimed in claim 1, wherein the aldehyde of the formula II is acrolein, 2-buten-1-al, 2-methyl-2-buten-1-al, 3-methyl-2-buten-1-al, 2-methyl-4-methoxy-2-buten-1-al, 2-methyl-4-methoxy-2-buten-1-al or 3-isopropyl-2-buten-1-al.

3. A process as claimed in claim 1, wherein the alcohol is 2-propen-1-ol, 2-buten-1-ol, 2-methyl-3-buten-2-ol, 3-methyl-2-buten-1-ol, geraniol or 2-methyl-2-propen-1-ol.

4. A process as claimed in claim 1, wherein the fraction of the reactants recovered in the first evaporation stage is added in the upper part of the reaction column, and the fraction of reactants recovered in the second evaporation stage is added to the lowest stage of the reaction column.

5. A process as claimed in claim 1, wherein the acetal is concentrated to a concentration of from 30% by weight to 99.9% by weight.

6. A process as claimed in claim 1, wherein the amount of the reactants recovered in the first evaporation stage is between 2 and 30 times the amount of freshly added aldehyde.

7. A process as claimed in claim 1, wherein the amount of freshly added alcohol is regulated such that the ratio of alcohol to aldehyde is between 1 and 3.

8. A process as claimed in claim 1, wherein a nonvolatile acid is added in the upper part of the distillation column.

9. A process as claimed in claim 1, wherein the acid in the lower part of the distillation column or in the evaporation stages is removed by neutralization or ion exchange.

10. A process as claimed in claim 1, wherein catalytically active solids are arranged in the reaction column.

11. A process as claimed in claim 1, wherein the amount of reflux is 200 to 50 000 kg per 1000 kg of aldehyde.

12. A process as claimed in claim 1, wherein the head pressure of the column K1 is between 2 mbar and 400 mbar.

13. A process as claimed in claim 1, wherein the temperature in the reactor C1 is between −20° C. and 100° C.

14. The process of claim 12 wherein the pressure is chosen such that the condensation temperature is above 0° C. at the head.

* * * * *